United States Patent [19]

Verlander et al.

[11] 4,192,798

[45] Mar. 11, 1980

[54] RAPID, LARGE SCALE, AUTOMATABLE HIGH PRESSURE PEPTIDE SYNTHESIS

[75] Inventors: Michael S. Verlander, Del Mar; William D. Fuller, Lakeside; Murray Goodman, La Jolla, all of Calif.

[73] Assignee: BioResearch, Inc., Farmingdale, N.Y.

[21] Appl. No.: 962,334

[22] Filed: Nov. 20, 1978

[51] Int. Cl.² ............................................. C07C 103/52
[52] U.S. Cl. .................... 260/112.5 R; 260/112.5 TR; 260/112.5 S; 260/112.5 T; 260/112.5 LH
[58] Field of Search ............... 260/112.5 R, 112.5 TR

[56] References Cited

U.S. PATENT DOCUMENTS

| | | | |
|---|---|---|---|
| 3,531,258 | 9/1970 | Merrifield et al. | 260/112.5 R |
| 3,557,077 | 1/1971 | Brunfeldt et al. | 260/112.5 R |
| 3,715,190 | 2/1973 | Park et al. | 260/112.5 R |
| 4,062,815 | 12/1977 | Hughes et al. | 260/112.5 R |

*Primary Examiner*—Delbert R. Phillips
*Assistant Examiner*—Blondel Hazel
*Attorney, Agent, or Firm*—Larson, Taylor and Hinds

[57] ABSTRACT

In the method for the synthesis of a polypeptide chain on an insoluble solid support wherein an amino acid is introduced into a reactor packed with an insoluble solid support containing substituent groups reactive with said amino acid, coupling said amino acid to said support by condensation reaction with said reactive substituent groups, introducing a second similar or dissimilar amino acid into said reactor and coupling said second amino acid to said first amino acid and repeating the process until the desired polypeptide is obtained, the improvement wherein a high pressure flow system is used and the reaction pressure in said reactor during said synthesis is at least 200 psi up to 10,000 psi or more, in order to obtain rapid reactions and quantitative yields of the desired products.

10 Claims, 1 Drawing Figure

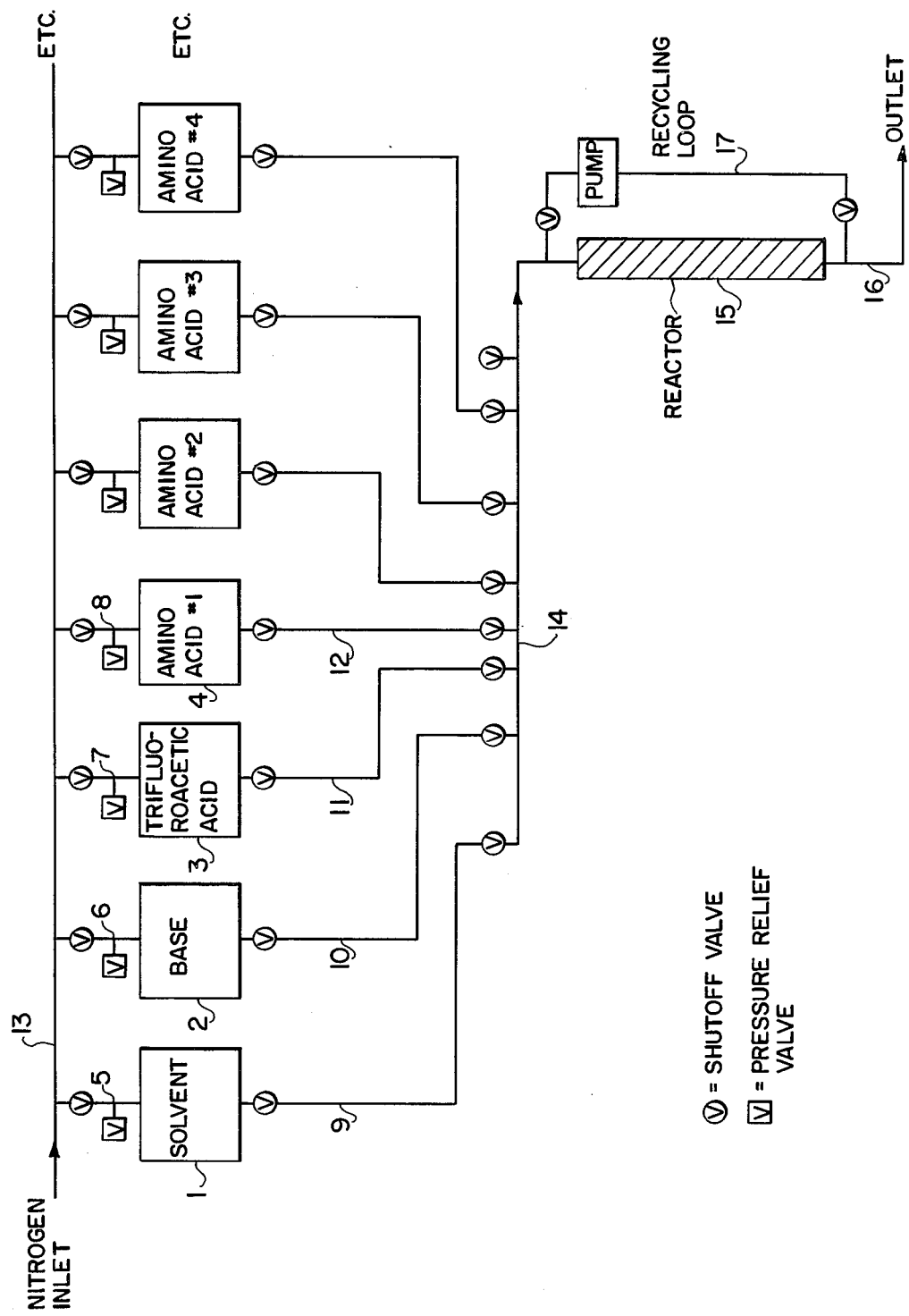

RAPID, LARGE SCALE, AUTOMATABLE HIGH PRESSURE PEPTIDE SYNTHESIS

FIELD OF THE INVENTION

This invention relates to the synthesis of peptides, polypeptides and proteins. More particularly, the invention relates to an improvement in peptide, polypeptide and protein synthesis wherein the peptide, polypeptide or protein is "grown" on an insoluble support or carrier by a series of stepwise coupling reactions.

BRIEF DESCRIPTION OF PRIOR ART

Classically, sequential polypeptides have been prepared by extremely laborious techniques wherein the intermediates have been isolated after the addition of each amino acid moiety. This has made the synthesis complicated and the preparation of long chain polypeptides nearly impossible because of low yields and/or racemization or other side reactions. In 1963, Merrifield (J. Am. Chem. Soc., 85, 2149) and Letsinger and Kornet (J. Am. Chem. Soc., 85, 2045) suggested the use of an insoluble polymer support for the growing peptide chain. This process permitted the purification of the growing peptide chain, prepared by classical synthetic methods, without isolating the intermediate. In such a process the insoluble support is provided a reactive substituent group as by chloromethylation, carboxylation, hydroxymethylation, etc. and a protected amino acid coupled thereto either via the amino or carboxyl group. Then using a series of deprotection and coupling reactions the peptide is synthesized in a stepwise manner on the insoluble support. Although in principle the peptide may be assembled either from the amine or the carboxyl terminus, in practice the latter is preferred, mainly because of lower extents of racemization when N-urethane protected, carboxyl activated amino acids are used for coupling reactions. After each deprotection step the insoluble support and its appended peptide chain are neutralized if necessary and washed before the addition of the next amino acid residue. Finally, the polypeptide is removed from the solid support by use of a suitable cleaving reagent, and any necessary deprotections completed. The final peptide is then subjected to extensive purification.

Although the solid-phase method of peptide synthesis, originally developed by Merrifield, has revolutionized the field of synthetic peptide chemistry, the method is complicated by many problems, especially when applied to large peptides (>10 amino acids). For example, the reactive sites on the insoluble supports employed in the syntheses are located on and within the support at varying degrees or depths of accessibility. Because of shrinkage and swelling of the resin during a normal synthetic procedure, the number of "inaccessible sites" will change throughout the procedure. This means that a reactive site which is inaccessible during one particular cycle may in practice become accessible during a subsequent cycle. Because of the heterogeneous nature of the reaction sites on the support and their variability with time, reactions in the Merrifield synthetic procedure are often incomplete and unpredictable even though a substantial excess of the amino acid reactant is used. When very long polypeptide chains are synthesized this failure to obtain 100% reaction during every step of the synthesis gives rise to a large variety of "contaminant" polypeptides with "failure sequences" (i.e. sequences containing deletion or alteration of one or more amino acid residues). Since these "contaminant" polypeptides are similar to the desired product they are difficult to separate and reduce the yield of desired peptide.

Another drawback of the Merrifield method is that long reaction times are ordinarily required to complete the coupling reaction. Depending on the amino acid reactant used, the addition of a single residue to the sequence may take anywhere from 3 to 24 hours or more. Consequently, it is difficult to do more than 2 or 3 couplings during a 24 hour period. These long coupling times may also lead to many undesirable side reactions which, after many coupling reactions, result in a marked decrease in yields and purity of the desired peptide. These problems tend to limit the usefulness of the Merrifield synthesis to peptides with chainlengths of about 10 to 15 amino acids.

OBJECTS OF THE INVENTION

It is an object of the invention therefore to provide a method for the synthesis of polypeptides and proteins which overcomes the aforementioned problems associated with the Merrifield method or approach.

More specifically, it is an object of the invention to provide a method for the synthesis of polypeptides and proteins which offers extraordinarily rapid reaction rates compared to conventional solid-phase reactions.

Yet another object of the invention is to provide an automatable method wherein long chain polypeptides of greater than 20 amino acids can be prepared on a large scale, with little, if any, side reactions.

A further object of the invention is to provide a method wherein coupling reactions are complete at every stage of the synthesis regardless of the sequence or structure of the peptide so that the polypeptide or protein product of desired chain length or size requires minimum purification or in many instances no purification after cleavage from the support.

SUMMARY OF THE INVENTION

These objects are obtained by an improvement in the method for the synthesis of polypeptide or protein chains on an insoluble solid support wherein an amino acid is passed in a continuous flow through a reactor packed with an insoluble solid support containing substituent groups relative with said amino acid and coupled to said support by condensation reaction with said reactive substituent groups, a second similar or dissimilar amino acid is passed in a continuous flow through said reactor and coupled to said first amino acid and the process repeated until the desired polypeptide is obtained, which improvement comprises conducting the reaction in a flow reactor under pressures of at least 200 psi, preferably at least 1,000 psi up to 10,000 psi or more. In general, the flow rate of the reactants and reagents employed will fall in the range of 4 to 50 ml per minute or more depending on the size of the reactor used.

In a preferred aspect of the invention the first amino acid passed through the reactor packed with the insoluble support containing substituent groups reactive with said amino acid, is a protected amino acid. In accordance with this aspect of the invention a protected amino acid is coupled to said support by condensation reaction with said substituent groups, said coupled first amino acid is deprotected by passing a deprotecting agent through the flow reactor, a second similar or dissimilar protected amino acid is passed through said reactor and coupled to said first coupled amino acid, said coupled second amino acid is deprotected and the process repeated until the desired polypeptide is obtained, the improvement being that during said synthesis the reactants and reagents are passed through the reactor in a continuous flow and the reaction pressure in said reactor is at the defined elevated pressures in order to obtain rapid reactions and quantitative yields of the desired products.

It has been surprisingly found that conducting the steps of the synthesis in such a flow system and also under elevated pressures of at least 200 psi ensures complete coupling reactions between the amino acids introduced and all of the available reactive sites on or within the insoluble support within a greatly reduced time period which is independent of the sequence of the polypeptide or protein. Similarly, it has been found that 100% deprotection is effected when this aspect of the invention is employed. In addition, any wash or neutralization operations that may be employed are greatly facilitated. As a consequence, formation of by-product polypeptides, that is, polypeptides of shorter chain lengths or polypeptides formed as a result of rearrangement of the activated amino acids or other side reactions is completely eliminated. Quantitative yields of desired long-chain polypeptides and proteins are therefore made possible and the separation or purification problems that ordinarily plague conventional solid-phase synthesis in this regard are overcome. Also, the reaction rates achieved under the high pressure synthesis of the invention compared to conventional solid-phase polypeptide coupling reactions are unexpectedly rapid. For example, coupling reactions which typically take hours by the conventional procedures are completed in minutes. Such rapid rates of reaction result in the complete elimination of undesirable side reactions that occur because of the tendency of activated amino acids to decompose or rearrange during the long reaction times required for conventional synthetic procedures.

A logical extension of the method described herein is the application of high pressure to other sequential synthetic procedures. These include sequential polynucleotide synthesis and polysaccharide synthesis. In a similar manner, high pressure may be used to increase rates and efficiencies of reactions in sequencing of polypeptides, proteins and nucleic acids. The use of high pressures in accordance with the teachings of the invention increases rates of reaction and also drives the reactions to completion, the both of which combine to result in rapid synthesis of pure materials in complicated, repetitive, sequential synthetic procedures.

DETAILED DESCRIPTION OF THE INVENTION

It should be understood that the term "polypeptides" as used in the specification and the appended claims is meant to include peptides and proteins.

In the synthesis of the present invention, an insoluble solid support or matrix, advantageously in bead form, such as any of the conventional solid-phase polymeric substrates conventionally employed for the synthesis of polypeptides can be utilized. Typical of such polymeric resins are crosslinked polystyrene resins, glass beads, clays, celite, crosslinked dextran, and similar insoluble solid supports which either naturally contain reactive sites for coupling with the amino acid components or which can be provided with such reactive sites. Insoluble supports particularly preferred are chloromethylated, crosslinked polystyrene resins, hydroxymethylated, crosslinked polystrene resins, benzhydrylamine resins and the like. The crosslinked polystyrenes are normally copolymers of styrene and a crosslinking agent preferably formed by way of a pearl or bead polymerization process using an aqueous suspension system. Preferred crosslinking agents for preparation of the crosslinked polystyrene resins include divinyl compounds such as para-divinylbenzene, meta-divinylbenzene, vinylcyclohexane, butadiene, and the like.

Several preliminary operations are necessary before the synthesis of a peptide can be started. First, the supporting resin containing the C-terminal amino acid of the proposed peptide chain must be prepared. This can be accomplished in the same reactor and under the high pressure conditions of the present invention. However, since the attachment of the first (i.e. C-terminal) protected amino acid residue involves a relatively longer reaction time than the subsequent amino acid coupling reactions, it is preferred to complete the first attachment beforehand and store the C-terminal amino acid substituted resin until needed.

The insoluble solid support containing the C-terminal amino acid may be prepared for instance by esterifying a suitably protected amino acid with the reactive site or substituent group on the insoluble support such as chloromethylated or hydroxymethylated crosslinked polystyrene resins. The esterification reaction is accomplished directly with the chloromethylated resin or via suitable activation of the amino acid in the case of the hydroxymethylated resin. There are a considerable number of protecting groups for terminal reactive amino groups which have been employed in peptide synthesis but the protecting groups of choice have been the t-butyloxycarbonyl group and the benzyloxycarbonyl group. After the first C-terminal amino acid is coupled to the support, the resulting product is commonly analyzed using standard procedures such as quantitative amino acid analysis to determine the amino acid content for the purpose of calculating the amounts of subsequent amino acid reactants and deprotecting agents to be used in the synthesis.

The thus-prepared C-terminal amino acid-containing support is packed into a suitable continuous flow reactor. The reactor may take any desired shape or form so long as it is capable of withstanding the high pressures under which the synthesis of the present invention is conducted. The preferred reactors, however, are column reactors having an inlet and an outlet so as to maximize the contact time between solvent or reactants and the growing peptide chains on the resin, thus maximizing the efficiency of the process.

The remaining sythesis to form the desired polypeptide sequence is carried out as follows. Before coupling of the second amino acid residue can take place, the first residue already on the support must be deprotected. Deprotection of the first amino acid residue on the resin as well as on each of the subsequently coupled amino acid residues can be carried out by pumping through the reactor an appropriate deprotecting agent. The deprotecting agents employed for this purpose are well known to those of ordinary skill in the peptide synthesis art and the particular deprotecting agent employed in any given instance will depend of course upon the protecting group on the amino acid/resin. For example, if the protecting group is t-butyloxycarbonyl, trifluoroacetic acid, methanesulfonic acid or hydrochloric acid in a suitable solvent such as dioxane or dichloromethane may be used. On the other hand, if the protecting group is benzyloxycarbonyl, acidic solvolysis is the preferred method of deprotection. The concentrations of the particular deprotecting agent in the solvent will vary depending again upon the particular protecting agent employed but will ordinarily range from about 5 to 50% by volume. A sufficient volume of deprotecting agent is pumped through the reactor over a period of time sufficient to effect complete removal of the protecting groups. Frequently, multiple reactor volumes (for example 2–5 column volumes over a period of 5–30 minutes) of the solution containing the deprotecting agent are passed through the reactor to ensure complete removal of the protecting group.

After the deprotecting step, the resin is washed with a suitable solvent, normally the solvent in which the deprotecting agent was dissolved, in order to remove excess deprotecting agent. If the deprotecting agent is an acid the peptide on the resin must be neutralized by washing with an appropriate base such as triethylamine in a solvent such as dichloromethane. Any excess triethylamine and triethylammonium chloride, trifluoroacetate, or bromide formed may be removed by repeated washings with a suitable solvent such as dichloromethane or dimethylformamide. The free amine, thus prepared, is now ready for coupling with the next protected amino acid.

The next N-protected amino acid is first activated, that is, converted into a reactive form, for instance, by converting the amino acid into an active ester or anhydride or by activation with dicyclohexylcarbodiimide, carbonyldiimidazole or other activating agents. A solution of the activated protected second amino acid is then passed into and through the reactor packed with the support now containing an unprotected C-terminal amino acid. In general, an excess of the activated, protected amino acid per equivalent of the first amino acid on the resin is employed although the excess required may be limited by recycling solutions through the column. Again the common practice is to pass more than one reactor volume of the activated, protected amino acid through the reactor to ensure complete reaction. It should be understood that any of the conventional methods of activating amino acids for the purpose of coupling with another amino acid may be applied to this method. These procedures should be well-known to anyone skilled in the art of peptide chemistry.

After the coupling of the second protected amino acid to the first amino acid, the attached protected amino acid is then deprotected, neutralized (if necessary) and washed as described above before coupling of the next amino acid derivative is effected. This procedure is repeated until the desired sequence of amino acids has been assembled on the insoluble support.

While the above described methods progress from the carboxyl terminus end toward the amine terminus end of the peptide, it should be understood that the reverse direction of synthesis, that is, from amine terminus to carboxyl terminus can be employed. For instance, a prepared or selected insoluble support having sites such as alkyloxycarbonyl or aryloxycarbonyl chloride groups, activated carboxyl groups, etc., reactive with the amine group of an amino acid can be used.

The entire series of coupling reactions in the above-described methods, from the second amino acid, (and if desired the first amino acid) to the last is conducted under a reactor pressure of at least 200 psi, up to 10,000 psi or more, preferably at least about 1,000 psi. Reactor pressures of this level can be generated by use of commercial pressurizing equipment and methods. For example, any of the commercially available high pressure reciprocating pumps capable of generating the required pressures can be used and the reactants, reagents and wash solvents pumped directly into and through the reactor.

Alternatively, the reactants, reagents and wash solvents may be pumped through the reactor by means of pressurization with an inert gas such as nitrogen and the pressure in the reactor regulated by controlling the volume of inert gas released to transfer the reactants, reagents and wash materials into and through the reactor.

A simple method of delivering solvents and reagents under the high pressure required for this method involves the use of a conventional high pressure liquid chromatography apparatus. The columns of such a system can serve as reactors for the polypeptide synthesis and the high pressure pump generally found in such an apparatus may be easily adapted to pump reagents and solvents through the column reactor. However, such an apparatus is limited to small scale (less than 1 gram of peptide) synthesis since the maximum possible flow rates in such a system are too low (generally less than 10 ml per minute) for larger scale synthesis.

The completed peptide sequence can be removed from the insoluble support by any of the standard methods as, for instance, by cleavage with anhydrous hydrogen fluoride, transesterification, aminolysis, etc. This cleavage is most conveniently accomplished by extruding the peptide-support from the reactor and treating it with anhydrous hydrogen fluoride at atmospheric pressure. However, the cleavage may also be carried out in the reactor and under the high reactor pressures of the invention provided the reactor is resistant to hydrogen fluoride. An example of such a reactor is a Kel F column. Such a reactor is not required for cleavage methods other than hydrogen fluoride.

After cleavage, the resulting peptide is found to be remarkably homogeneous and to require no or minimal purification. Because of the very low contamination of by-products overall yields are found to be surprisingly high and whatever purification is necessary can be carried out with relative ease. Such purifications are preferably carried out by partition chromatography, ion exchange chromatography or a combination of both.

Illustrations of peptides, polypeptides and proteins which can be obtained by the method of the invention are enkephalins, angiotensin, oxytocin, vasopressin, luteinizing hormone releasing hormone, somatostatin, gastrin, insulin, glucagon, ribonuclease, endorphins, etc.

The following examples are included to further illustrate the present invention.

EXAMPLE I t-Butyloxycarbonyl-(phenylalanyl)$_3$-glycine methyl ester

A high pressure liquid chromatography pump (Waters Associates Model 6000A) was used for this experiment. Approximately 4 grams of 1% crosslinked polystyrene (200–400 mesh) containing 0.48 millimoles/gram of t-butyloxycarbonyl glycine was swollen in dichloromethane (wet volume 25–30 ml). The crosslinked polystyrene was a copolymer of styrene and approximately 1% divinylbenzene in bead form and the t-Boc-glycine-polystyrene resin was derived from the corresponding chloromethylated crosslinked polystyrene by esterification with t-butyloxycarbonyl glycine.

The swollen t-Boc-glycine-polystyrene resin was packed into a stainless steel column (0.8×60 cm) and the protecting group (t-Boc) was removed by pumping 5 column volumes of 10% (v/v) trifluoroacetic acid (TFA) in dichloromethane through the column. Excess TFA was removed by washing with 3-5 column volumes of dichloromethane and the TFA salt of the resin-amino acid neutralized by washing with 2 column volumes of triethylamine in dichloromethane (10% v/v). The neutralization was followed by a washing with 3-5 column volumes of dichloromethane.

A second amino acid, i.e. t-Boc-pheylalanine, was activated via mixed anhydride formation using isobutyl chloroformate and triethylamine. Two column volumes of the solution of the activated second amino acid (10 millimoles/100 ml in dichloromethane) were pumped through the column. Excess reactant solution was removed by washing with 3-5 column volumes of dichloromethane.

The above sequence of reactions (deprotection, washing, neutralization, washing, coupling and washing) was repeated twice to give the desired tetrapeptide sequence, Boc-(Phe)$_3$-Gly-O-resin. The tetrapeptide was removed from the resin by transesterification by stirring overnight in methanol/triethylamine.

The yield of product was virtually quantitative and TLC data indicated that the product was extremely pure. Analysis of the reaction mixture revealed no peptide or amino acid derived contaminants.

The peptide synthesis took approximately 6 hours, excluding the coupling of the first amino acid (glycine) and cleavage of the completed product from the resin. In view of the limitations on flow rate provided by the pump (maximum flow rate≦9.9 ml per minute) the reaction time for this synthesis could not be shortened.

EXAMPLE II t-Butyloxycarbonyl-(phenylalanyl)$_3$-phenylalanine methyl ester

This tetrapeptide was prepared using the high pressure flow system diagrammatically illustrated in the accompanying drawing. In the high pressure flow system, nitrogen gas is used to pressurize the various reactants and reagents of the synthesis through the column reactor. The nitrogen gas is passed into reservoirs 1,2,3, and 4 provided with inlets 5,6,7 and 8, respectively and outlets 9,10,11 and 12, respectively. The inlets 5,6,7 and 8 connect with a common inlet line 13 and the outlet lines 9,10,11 and 12 with a common outlet line 14 that enters a reactor 15. The reservoirs 1,2,3 and 4 contain solvent (dichloromethane), base (triethylamine), trifluoroacetic acid and activated amino acid respectively. Other reservoirs and their accompanying inlet and outlet lines may be provided as shown for other amino acids used in the synthesis if desired. The reactor 15 contains an outlet line 16 and is equipped with a recycling loop 17.

Approximately 4 grams of 2% crosslinked polystyrene (200–400 mesh) containing 0.50 millimoles/gram of t-butyloxycarbonyl phenylalanine was swollen in dichloromethane (wet volume ~15 ml). The crosslinked polystyrene was a copolymer of styrene and approximately 2% divinylbenzene in bead form and the t-Boc-phenylalanine polystyrene resin was derived from the corresponding chloromethylated crosslinked polystyrene by esterification with t-butyloxycarbonyl phenylalanine.

The swollen t-Boc-phenylalanine polystyrene resin was packed into a stainless steel column reactor (0.8×32 cm) 15 and the protecting group (t-Boc) was removed by passing under nitrogen gas pressure five column volumes of 20% (v/v) trifluoroacetic acid (TFA) in dichloromethane from reservoir 3 through the column. Excess TFA was removed by washing with 3-5 column volumes of dichloromethane from reservoir 1 and the TFA salt of the resin amino acid neutralized by washing with 2 column volumes of triethylamine in dichloromethane (3% v/v) from reservoir 2. The neutralization was followed by washing with 3-5 column volumes of dichloromethane from reservoir 1.

A second amino acid, i.e. t-Boc-phenylalanine, was activated via mixed anhydride formation using isobutyl chloroformate and triethylamine. Two column volumes of the solution of the activated second amino acid (10 millimoles/100 ml in dichloromethane) from reservoir 4 were passed through the column under nitrogen gas pressure. Excess reactant solution was removed by washing with 3-5 column volumes of dichloromethane from reservoir 1.

The above sequence of reactions (deprotection, washing, neutralization, washing, coupling and washing) was carried out at a pressure of 1200 psi, and at a flow rate in the range of 4 to 30 ml per minute. The sequence of reactions was repeated twice more to give the desired tetrapeptide sequence, Boc-(Phe)$_4$-O-resin. The tetrapeptide was removed from the resin by transesterification by stirring overnight in methanol/triethylamine.

The yield of product was essentially quantitative and TLC data indicated that the product was remarkably pure. Analysis of the reaction mixture revealed no peptide or amino acid derived contaminants.

The peptide synthesis took approximately 3 hours, excluding the coupling of the first amino acid (phenylalanine) and cleavage of the completed product from the resin.

It is claimed:

1. In the continuous flow method for the synthesis of a polypeptide chain on an insoluble solid support wherein a protected amino acid is passed in a continuous flow through a flow reactor packed with an insoluble solid support containing substituent groups reactive with said protected amino acid, and coupled to said support by condensation reaction with said reactive substituent groups, a second similar or dissimilar protected amino acid is passed through said reactor in a continuous flow and coupled to said first amino acid and the process repeated until the desired polypeptide is obtained, the improvement comprising conducting the reaction in said flow reactor under a pressure of at least 200 psi.

2. The improvement of claim 1 wherein the reaction pressure is at least 1,000 psi.

3. The improvement of claim 2 wherein the reaction pressure is about 1,000 to 5,000 psi.

4. The improvement of claim 1 wherein the reactive substituent groups on said insoluble support are protected amino acids.

5. The improvement of claim 1 wherein said support is a crosslinked polystyrene in bead form.

6. In the method for synthesis of a polypeptide chain on an insoluble solid support wherein a first protected amino acid is passed through a reactor packed with an insoluble solid support containing substituent groups reactive with said protected amino acid and coupled to said support by condensation reaction with said substituent groups; said amino acid is deprotected by passing through said reactor a deprotecting agent, a second similar or dissimilar protected amino acid is passed through said reactor and coupled to said first coupled amino acid, said coupled second amino acid is deprotected by passing through said reactor a deprotecting agent and repeating the process until the desired peptide is obtained, the improvement wherein the reactants and reagents are passed through the reactor in a continuous flow under pressure of at least 200 psi.

7. The improvement of claim 6 wherein the reaction pressure is at least 1,000 psi.

8. The improvement of claim 7 wherein the pressure is about 1,000 to 5,000 psi.

9. The improvement of claim 6 wherein the reactive substituent groups on said insoluble support are protected amino acids.

10. The improvement of claim 7 wherein the insoluble support is a crosslinked polystyrene in bead form.

* * * * *